US009417340B2

(12) United States Patent
Basu et al.

(10) Patent No.: US 9,417,340 B2
(45) Date of Patent: Aug. 16, 2016

(54) COMPACT GEOMETRY CT SYSTEM

(75) Inventors: Samit Kumar Basu, Fremont, CA (US);
Pedro Andres Garzon, Santa Clara, CA (US); Jed Douglas Pack, Glenville, NY (US)

(73) Assignee: MORPHO DETECTION, LLC, Newark, CA (US)

( * ) Notice: Subject to any disclaimer, the term of this patent is extended or adjusted under 35 U.S.C. 154(b) by 463 days.

(21) Appl. No.: 13/543,255

(22) Filed: Jul. 6, 2012

(65) Prior Publication Data

US 2014/0010343 A1    Jan. 9, 2014

(51) Int. Cl.
*G01T 1/29* (2006.01)
*G01N 23/04* (2006.01)
*G01V 5/00* (2006.01)

(52) U.S. Cl.
CPC .......... *G01T 1/2985* (2013.01); *G01N 23/046* (2013.01); *G01V 5/005* (2013.01); *G01N 2223/419* (2013.01); *Y10T 29/49826* (2015.01)

(58) Field of Classification Search
CPC ..... G01N 23/00; G01N 23/04; G01N 23/046; G01N 2223/419; G01V 5/02; G01V 5/04; G01V 5/005; G01V 5/0008; G01V 5/12; A61B 6/00; A61B 6/032; A61B 6/06; A61B 6/4028; A61B 6/4233; A61B 6/4291; B23P 11/00; G01T 1/2985; Y10T 29/49826
USPC .............. 378/15, 16, 19, 20, 21, 57, 62, 98.8, 378/114, 115, 116, 195, 196, 197, 198, 205, 378/208
See application file for complete search history.

(56) References Cited

U.S. PATENT DOCUMENTS

| | | | |
|---|---|---|---|
| 3,924,129 A * | 12/1975 | LeMay | .......................... 382/131 |
| 3,973,128 A | 8/1976 | LeMay | |
| 4,060,991 A | 12/1977 | Reese | |
| 4,160,911 A * | 7/1979 | Hounsfield | ...................... 378/19 |
| 4,228,505 A | 10/1980 | Wagner | |
| 4,670,840 A | 6/1987 | Freundlich | |
| 4,748,645 A | 5/1988 | Donges et al. | |
| 5,912,938 A | 6/1999 | Dobbs et al. | |
| 6,175,611 B1 | 1/2001 | Melen et al. | |
| 6,301,326 B2 | 10/2001 | Bjorkholm | |
| 6,975,699 B2 | 12/2005 | Kresse | |
| 7,016,459 B2 | 3/2006 | Ellenbogen et al. | |
| 7,039,154 B1 | 5/2006 | Ellenbogen et al. | |
| 7,116,811 B2 | 10/2006 | Leveau-Mollier | |
| 7,123,681 B2 | 10/2006 | Ellenbogen et al. | |
| 7,139,362 B2 | 11/2006 | Heismann et al. | |
| 7,164,747 B2 | 1/2007 | Ellenbogen et al. | |
| 7,224,765 B2 | 5/2007 | Ellenbogen | |
| 7,352,841 B2 | 4/2008 | Ellenbogen et al. | |

(Continued)

OTHER PUBLICATIONS

Goldman, Principles of CT and CT Technology, Sep. 2007, J. Nucl. Med. Technol. vol. 35, No. 3, p. 125.*

*Primary Examiner* — Glen Kao
(74) *Attorney, Agent, or Firm* — Armstrong Teasdale LLP

(57) ABSTRACT

An imaging system is provided. The imaging system includes a rotating gantry. An x-ray source is mounted to the gantry. The system also includes a plurality of interchangeable x-ray detector modules is mounted to the gantry, opposite the x-ray source. The plurality of interchangeable detector modules includes a first detector module mounted at a first distance from the x-ray source and a second detector module mounted at a second distance from the x-ray source. The first distance is different from the second distance.

18 Claims, 15 Drawing Sheets

(56) References Cited

U.S. PATENT DOCUMENTS

| | | |
|---|---|---|
| 7,440,537 B2 | 10/2008 | Ellenbogen et al. |
| 7,474,728 B2 | 1/2009 | Schlomka et al. |
| 7,474,735 B2 | 1/2009 | Spahn |
| 7,623,618 B2 | 11/2009 | Stierstorfer |
| 7,676,073 B2 | 3/2010 | Hamill et al. |
| 7,711,082 B2 | 5/2010 | Fujimoto et al. |
| 7,912,261 B2 | 3/2011 | Hornig |
| 2004/0120454 A1* | 6/2004 | Ellenbogen et al. ............ 378/19 |
| 2004/0161074 A1* | 8/2004 | Kresse ............................ 378/19 |
| 2004/0195512 A1 | 10/2004 | Crosetto |
| 2004/0251420 A1* | 12/2004 | Sun .......................... 250/370.09 |
| 2005/0105687 A1* | 5/2005 | Heismann et al. ........... 378/98.8 |
| 2005/0169422 A1* | 8/2005 | Ellenbogen ...................... 378/57 |
| 2007/0104321 A1 | 5/2007 | Spahn |
| 2007/0230766 A1* | 10/2007 | Hornig .......................... 382/132 |
| 2008/0089478 A1* | 4/2008 | Hartick et al. .................. 378/57 |
| 2012/0051518 A1 | 3/2012 | Omote et al. |
| 2013/0343507 A1* | 12/2013 | Gregerson ........... A61B 6/4488 378/4 |

* cited by examiner

COMPACT GEOMETRY CT SYSTEM

BACKGROUND OF THE INVENTION

The embodiments described herein relate generally to x-ray computed tomography and, more particularly, to computed tomography systems having compact geometry and highly uniform resolution throughout the field of view ("FOV"). Embodiments described herein also relate to processes for correcting artifacts in image data collected by a computed tomography system.

In at least some known computed tomography ("CT") imaging systems, an x-ray source projects a fan-shaped or a cone-shaped beam towards an object to be imaged. The x-ray beam passes through the object, and, after being attenuated by the object, impinges upon an array of radiation detectors. Each radiation detector produces a separate electrical signal that is a measurement of the beam intensity at the detector location. During data acquisition, a gantry that includes the x-ray source and the radiation detectors rotates around the object.

Traditional designs for CT systems place the detectors on an arc that is centered on the focal spot. As a result, the ratio between the usable FOV and the outer diameter of the CT system is relatively small. A typical CT system capable of scanning an 85 centimeter opening is in excess of 200 centimeters in diameter. Additionally, CT systems of the prior art have a resolution that is highest at the center of the FOV and decreases toward the edges of the FOV.

Turning to the correction of artifacts in image data, it is known that ring artifacts due to detector errors affect CT systems. Methodologies for correcting those artifacts have been developed to correct slight non-linearities in the responses of neighboring, contiguous detector elements. However, such methodologies do not correct artifacts resulting from small, high density objects and edges as they transition through a differential scatter region in a CT system.

BRIEF DESCRIPTION OF THE INVENTION

In one aspect, an imaging system including a rotating gantry is provided. An x-ray source is mounted to the gantry. The system also includes a plurality of interchangeable x-ray detector modules is mounted to the gantry, opposite the x-ray source. The plurality of detector modules includes a first detector module mounted at a first distance from the x-ray source and a second detector module mounted at a second distance from the x-ray source. The first distance is different from the second distance.

In another aspect, a baggage scanning system is provided. The system includes a housing having a length, a first opening, and a tunnel. The first opening defines an entrance to the tunnel within the housing. The tunnel is oriented along the length of the housing. A conveyor is located within the housing and is oriented along the length of the housing. The system further includes a gantry rotatably mounted within the housing, around the conveyor. Further, the system includes an x-ray source mounted to the gantry. A plurality of interchangeable x-ray detector modules is mounted to the gantry, opposite the x-ray source. The plurality of detector modules includes a first detector module mounted at a first distance from the x-ray source and a second detector module mounted at a second distance from the x-ray source. The first distance is different from the second distance.

In another aspect, a method of mounting interchangeable x-ray detector modules in a gantry of a computed tomography system to provide a compact geometry is provided. The gantry includes a substantially annular frame having a mounting point for an x-ray source and a positioning rail located opposite the mounting point for the x-ray source. The positioning rail defines a plurality of attachment surfaces each corresponding to a mounting point for an interchangeable x-ray detector module. The interchangeable x-ray detector modules are adapted to mount to the attachment surfaces. The method includes mounting a first interchangeable x-ray detector module at a first mounting point located a first distance from the x-ray source. The method further includes mounting a second interchangeable x-ray detector module at a second mounting point located a distance from the x-ray source. The first distance is different from the second distance.

DETAILED DESCRIPTION OF THE INVENTION

Figure 1:
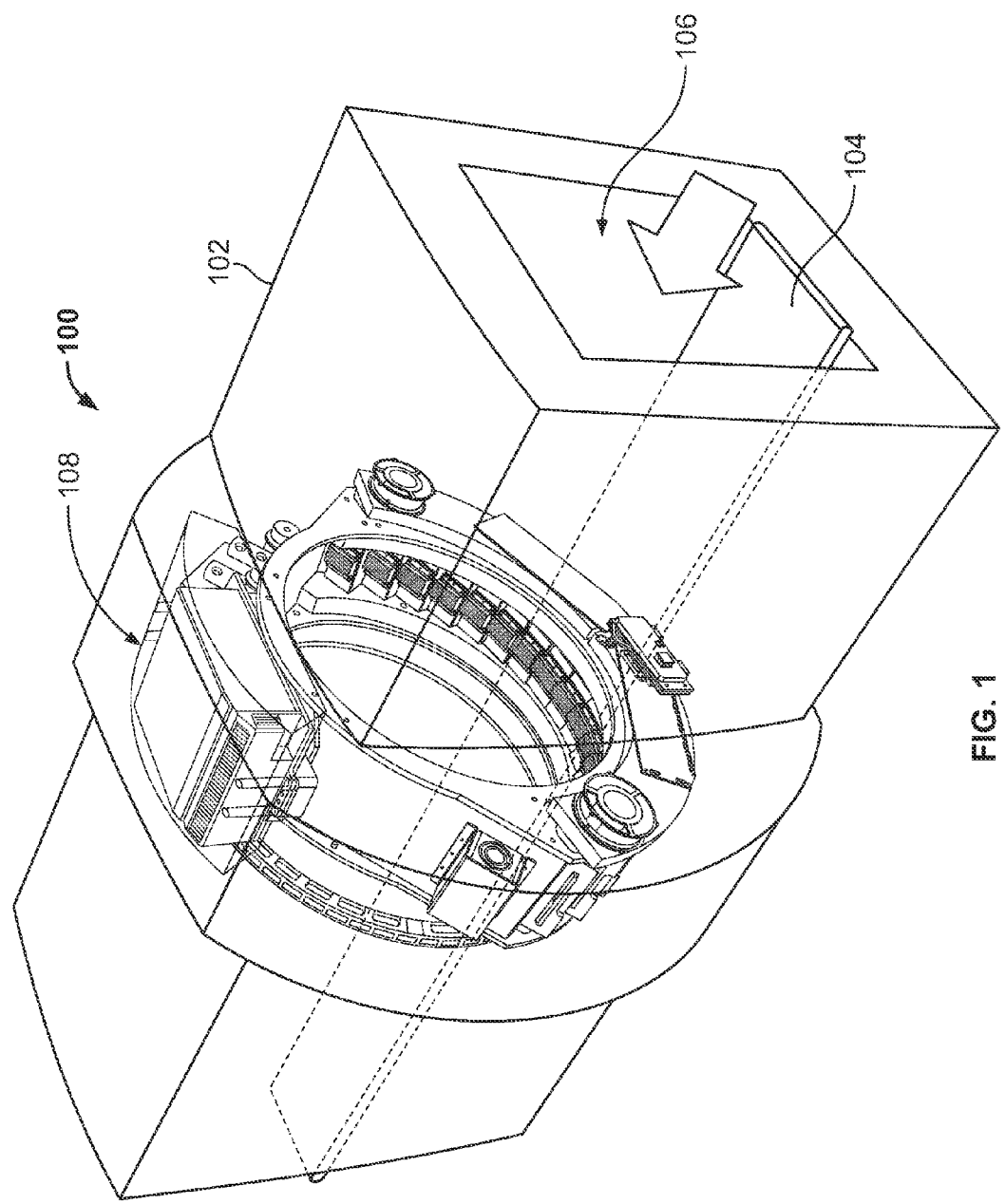
FIG. 1 is a perspective view of an imaging system in accordance with an exemplary embodiment of the present invention.

FIG. 1 is a perspective view of an imaging system 100 in accordance with an exemplary embodiment of the present invention. The imaging system 100 in this embodiment is a baggage scanning system, for viewing items in baggage passing through imaging system 100. For example, imaging system 100 may be used to detect contraband (e.g., explosives, drugs, weapons, etc.) located in the baggage. Imaging system 100 includes a tunnel 106 and a conveyor 104 extending through tunnel 106. Also included in imaging system 100 is a gantry assembly 108, shown in more detail in FIG. 2. In this embodiment, imaging system 100 has a housing 102 having a width of approximately 150 centimeters and a height of approximately 147 centimeters.

Figure 2:
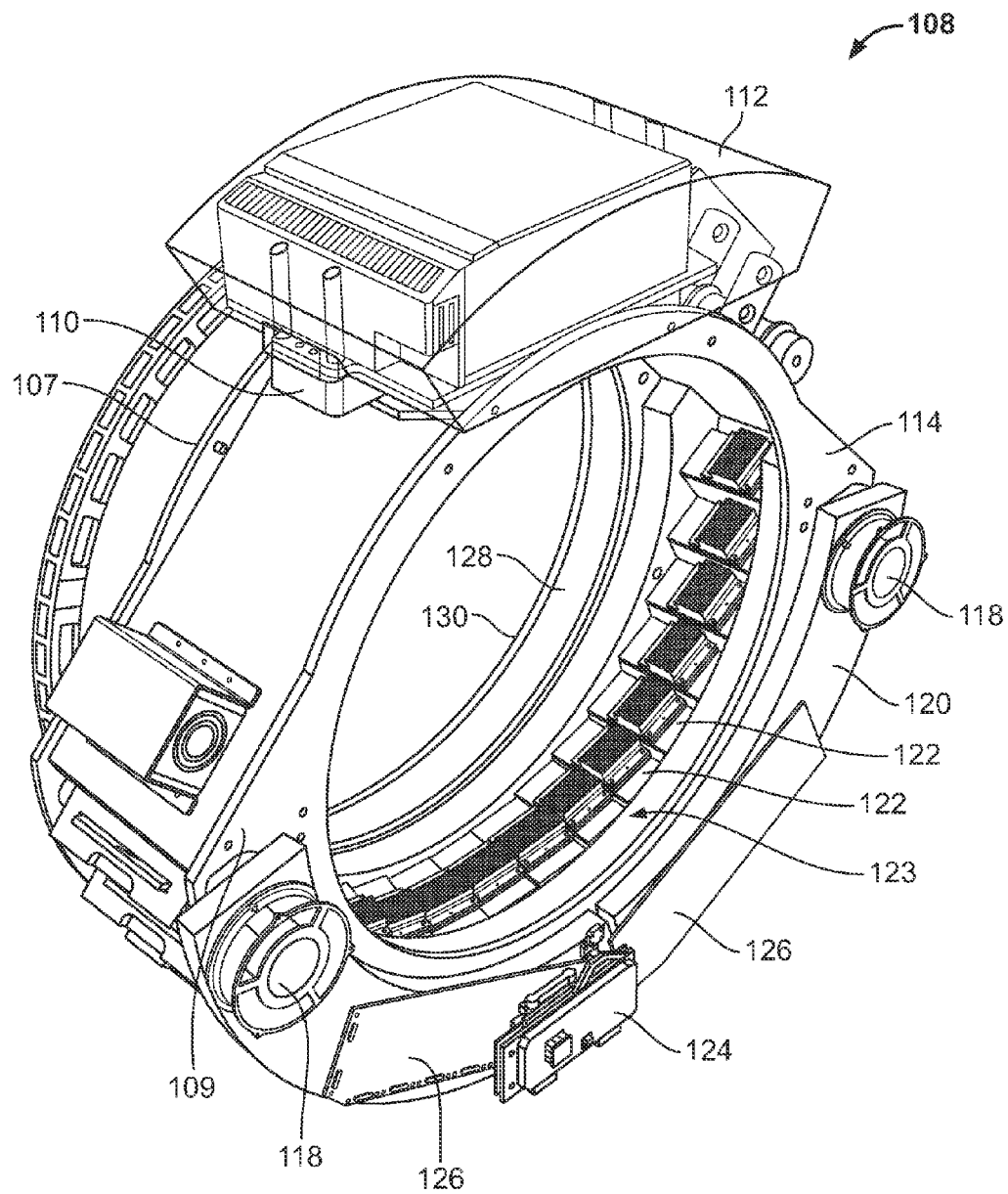
FIG. 2 is a perspective view of a gantry assembly in accordance with the exemplary embodiment of present invention.

FIG. 2 is a perspective view of gantry assembly 108 in accordance with the exemplary embodiment of the present invention. A radiation source 112, which emits x-rays, is mounted to a gantry frame 114 by an x-ray mount 110. In this embodiment, gantry frame 114 is a steel bolted structure with a bore of approximately 85 centimeters in diameter. The interior surface of gantry frame 114 is lined with lead. In this embodiment, x-ray mount 110 is cast steel with a lead cast window. X-ray mount 110 is configured to allow for position adjustment along an axis that is parallel to a length of tunnel 106 (the Z-axis).

On a first side 107 of gantry assembly 108, as shown in FIG. 2, are a bearing 128 and a slip ring 130. Bearing 128 allows gantry assembly 108 to rotate around an object to be imaged. In this exemplary embodiment, gantry assembly 108 is capable of rotating continuously, at approximately 150 rotations per minute. Slip ring 130 allows data signals and power to be transmitted between gantry assembly 108 and a remainder of imaging system 100, as will be appreciated by those skilled in the art. Attached to a second side 109 of gantry frame 114, opposite first side 107, is a plenum 120, which operates as a heat sink. Mounted to plenum 120 are global back planes 126, which contain electronics and circuitry for proper operation of gantry assembly 108, power management converter 124, for powering the components of gantry assembly 108, and fans 118 to transfer heat away from gantry assembly 108.

A plurality of detector modules 122 are arranged in an array 123, inside gantry frame 114. Detector modules 122 receive x-ray beams emitted from radiation source 112 and convert the x-ray beams to electrical signals representing image data. Detector modules 122 are positioned in the gantry assembly 108 with an axis of symmetry running from radiation source 112 to the center of central detector module 122. In alternative embodiments, there is an even number of detector modules, and an axis of symmetry runs from the radiation source to a point between two central detector modules. As explained below, detector modules 122 are arranged to increase an inner diameter of gantry assembly 108 relative to an outer diameter of gantry assembly 108, when compared to prior CT imaging systems. The benefit is that imaging system 100 is given a smaller footprint while maintaining or increasing the size of objects, such as baggage, that can be scanned.

Figure 3:
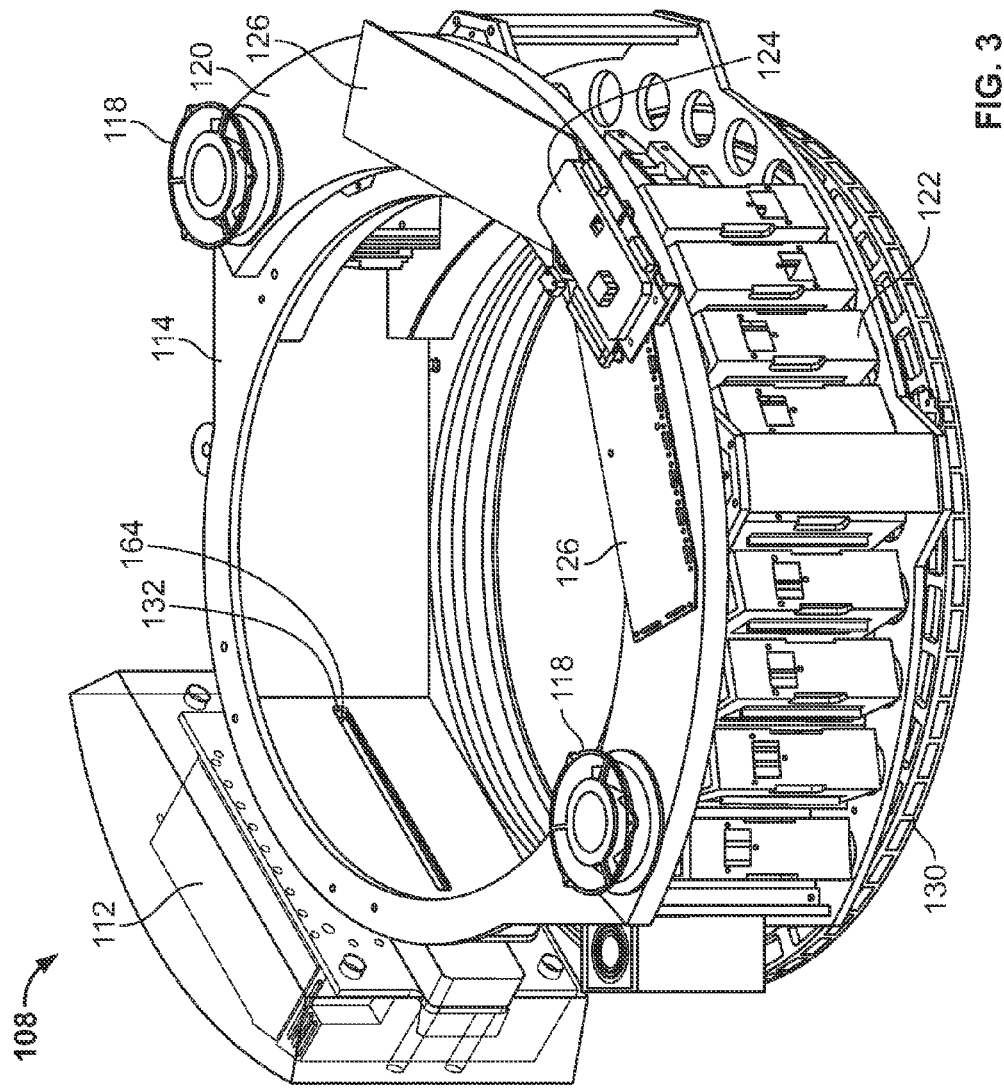
FIG. 3 is another perspective view of the gantry assembly in accordance with the exemplary embodiment.
Figure 4:
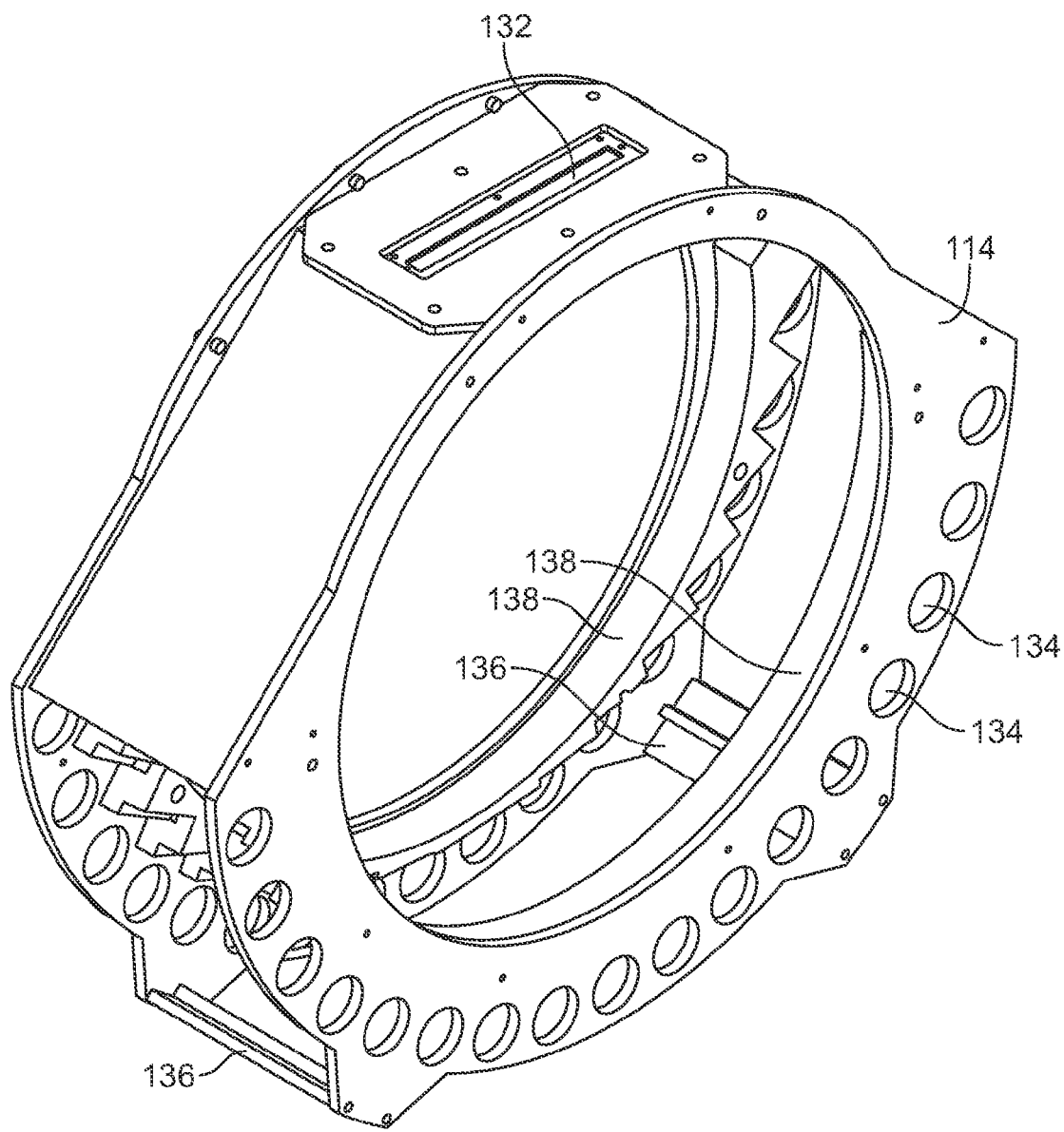
FIG. 4 is a perspective view of the gantry frame in accordance with the exemplary embodiment of the present invention.

FIG. 3 is another perspective view of gantry assembly 108 in accordance with the exemplary embodiment. An opening 132 in gantry frame 114 allows x-ray beams from radiation source 112 to be emitted into gantry assembly 108. The x-rays are emitted in a cone beam that intersects the entire tunnel 106. An x-ray seal with a pre-collimator 164 of x-ray attenuating material is located between radiation source 112 and opening 132. As shown in FIG. 3, slip ring 130 is attached to one side of gantry assembly 108 opposite plenum 120 and two global back planes 126 are mounted to plenum 120. Power management converter 124 is connected to global back planes 126. Fans 118 mounted to plenum 118 help transfer heat away from plenum 120 and gantry assembly 108 in general. Detector modules 122 are positioned such that during cone-to-parallel rebinning, resolution loss is minimized. As shown in FIG. 3, some detector modules 122 are removed to expose a portion of underlying gantry frame 114. In FIG. 4, discussed below, the gantry frame 114 is shown without any other components attached.

FIG. 4 is a perspective view of gantry frame 114 in accordance with the exemplary embodiment. Opening 132 allows x-rays from radiation source 112 to be emitted into gantry assembly 108 in a cone beam. Included on opposite interior sides of gantry frame 114 are positioning rails 138 that provide a mounting point for each detector module 122 in gantry assembly 108. Included along opposite outer sides of gantry frame 114 are cooling holes 134, to facilitate heat transfer away from gantry frame 114. Also included in gantry frame 114 are torsion force stiffeners 136, which provide structural support for gantry frame 114.

Figure 5:
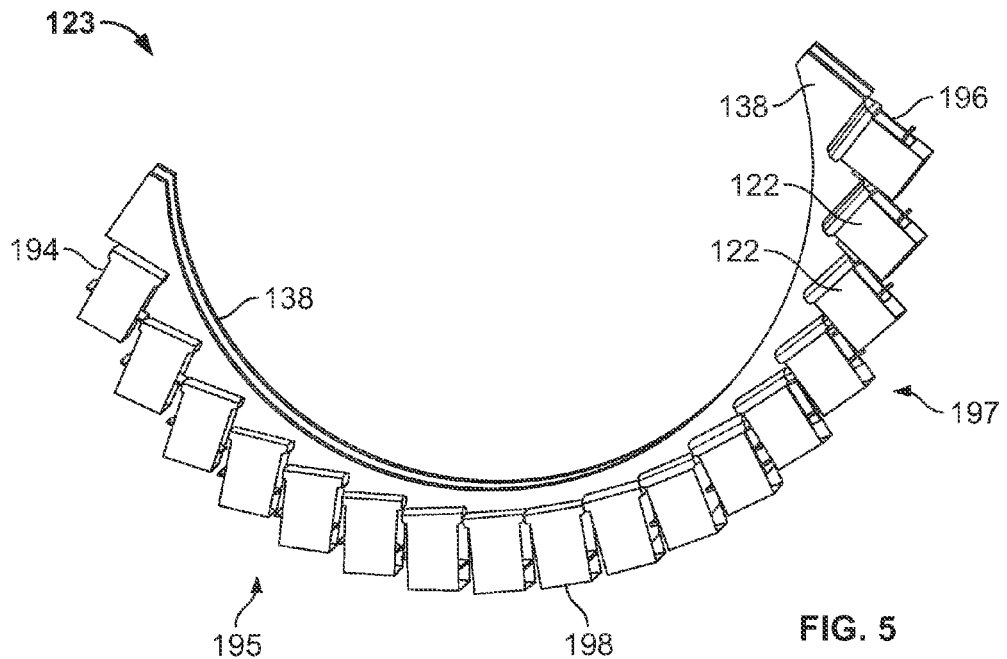
FIG. 5 is a perspective view showing an array of detector modules in accordance with the exemplary embodiment of the present invention.

FIG. 5 is a perspective view showing an array 123 of detector modules 122 in accordance with the exemplary embodiment of the present invention. Detector modules 122 are positioned along positioning rails 138. In this exemplary embodiment, 17 detector modules are included in the array 123. Array 123 includes a first end 194 and an opposite, second end 196. Additionally, array 123 is divided into a first half 195, extending from a center 198 of array 123 to first end 194, and a second half 197, extending from center 198 of array 123 to second end 196. Other embodiments may include fewer or more detector modules and the total number of detector modules may be odd or even. In the exemplary embodiment, one detector module 122 is located at center 198 such that it is directly opposite radiation source 112. Mirrored pairs of identical detector modules 122 extend outwards on either side. Detector modules 122 are gapped to allow for manufacturing tolerances in gantry assembly 108.

Figure 6:
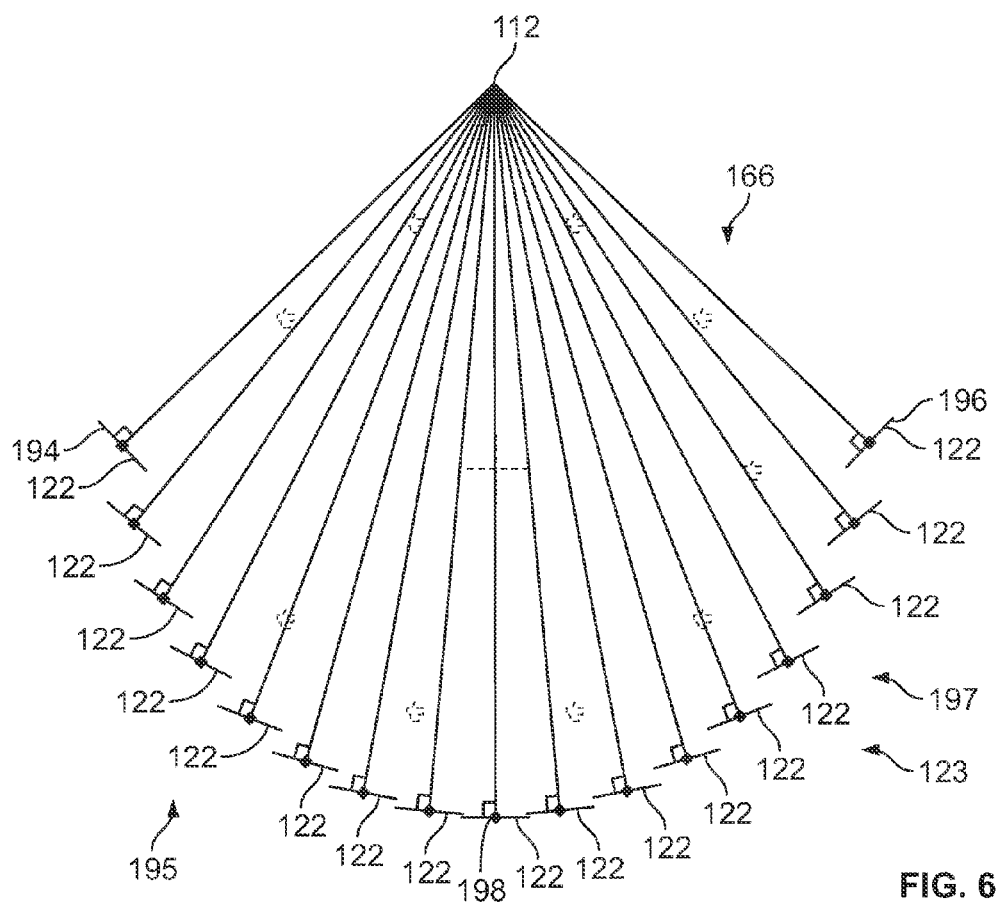
FIG. 6 is a diagram showing the paths of x-rays emitted by the radiation source to detector modules in accordance with the exemplary embodiment of the present invention.

FIG. 6 is a diagram showing x-ray beams 166 emitted by radiation source 112 to detector modules 122 in accordance with the exemplary embodiment. As can be seen, each detector module 122 is positioned so that the center of its collimator is normal to incident radiation bisecting detector module 122. Adjacent edges of adjacent detector modules 122 are angularly spaced from each other. The angular spacing of the centerlines of beams 166 bisecting adjacent detector modules 122 decreases moving from ends 194 and 196 of array 123 of detector modules 122 to the center 198.

Starting from detector module 122 at center 198, shown in FIG. 6, and moving outwards, each detector module 122 is a different distance from radiation source 112. That is, detector module 122 at center 198 is the furthest away from radiation source 112 and detector modules 122 along the first half 195 are closer to radiation source 112. Moving from center 198 towards first end 194, each successive detector module 122 is closer to radiation source 112 than the previous detector module 122. Each detector module 122 along first half 195 has a corresponding detector module 122 on second half 197, located at the same distance from radiation source 112. That is, each detector module 122, except detector module 122 located at center 198, is part of a mirrored pair. The result of this arrangement is a smaller outer diameter of gantry assembly 108 as compared to prior CT imaging systems which have a constant radiation source to detector distance (SDD). As a result of this arrangement of separate detector modules 122, the inner diameter of gantry assembly 108 is maximized relative to the outer diameter of gantry assembly 108.

Data from the x-ray beams must be mapped to a different geometry ("rebinned") once it is received by the detector modules, according to the following equation:

$$R_{m\alpha}(n\alpha)=P_{(m+n)\alpha}(D \sin n\alpha)$$

In the above equation, $\alpha$ represents the pitch of the data after rebinning in the column direction of the data. Further, in the above equation, n represents the rebinned data column index. In the equation above, D represents the isocenter distance and m represents the view angle of the data. $Rm\alpha$ represents parallel beam data, P represents fan beam data, $(m+n)\alpha$ represents angular interpolation, and D sin na represents detector interpolation. CT imaging systems of the prior art rebin from fan-to-parallel geometry. Such systems rebin in angle, first, for non-equispaced rays and rebin in detectors, second, for equispaced rays. However, the arrangement of detector modules described above produces beams that are nearly equispaced. Minor modifications to the source-to-detector distances through mimimax optimization result in beams that are even closer to being perfectly equispaced. As a result, the resolution loss from the second interpolation step can be minimized. This arrangement of detector modules 122 provides for a highly uniform resolution across the entire field of view of the imaging system.

Figure 7:
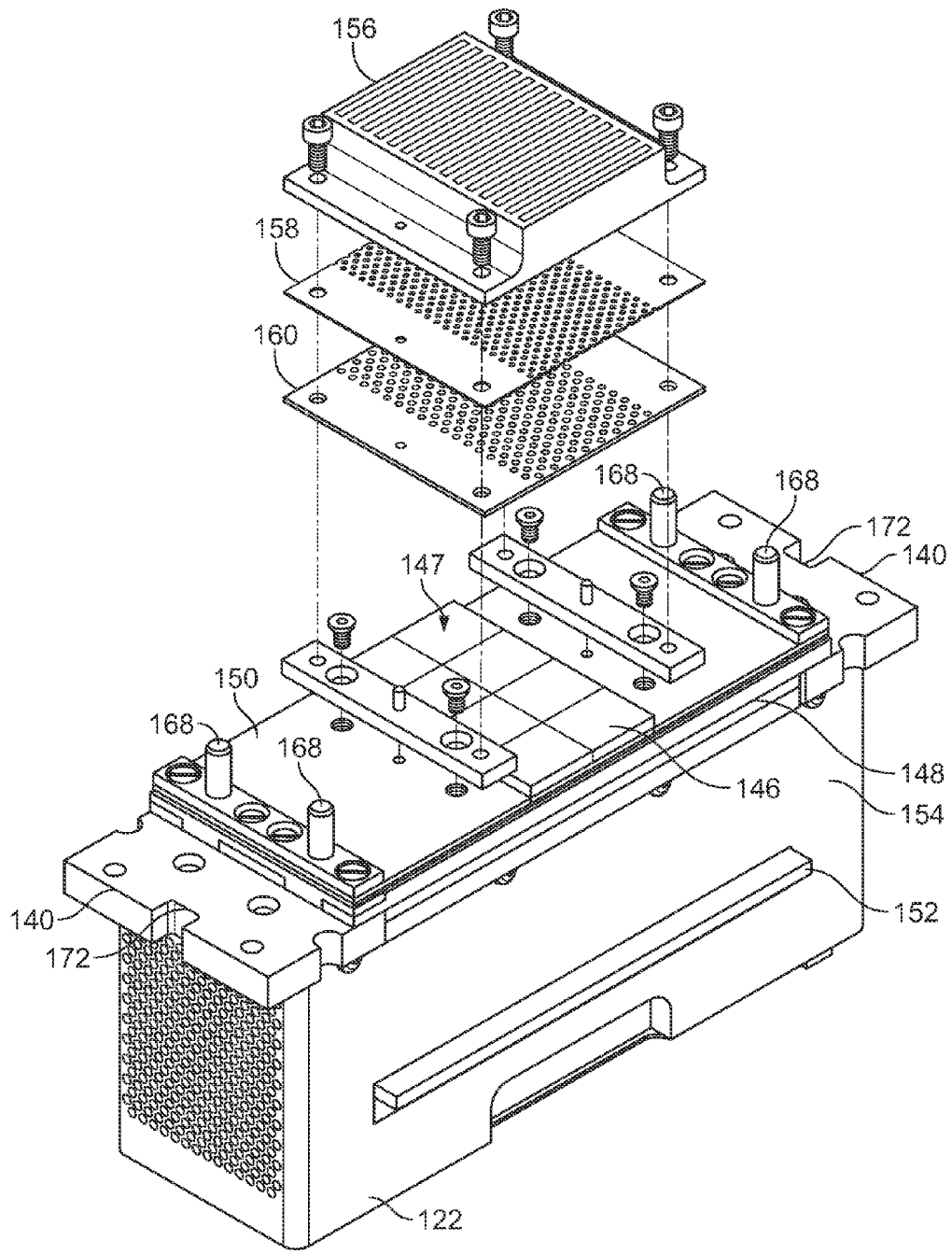
FIG. 7 is a partially exploded view of an exemplary detector module in accordance with the present invention.

FIG. 7 is a partially exploded view of an exemplary detector module 122. In the exemplary embodiment, every detector module 122 is identical and interchangeable with every other detector module 122. Each detector module 122 includes a one-dimensional collimator 156 that includes radiation-attenuating material, such as tungsten. In certain embodiments, collimator 156 also includes antimony and tin. Collimator 156 includes an array of fins, which in the exemplary embodiment, each have a minimum thickness of about 0.5 millimeters. Collimator 156 has a fixed focal length, and is about 20 millimeters in height. Collimator 156 mounts to substrate 150 on detector module 122. Also mounted to substrate 150 is a grid 147 of detector elements 146 that include scintillators which convert ionizing radiation into light, and photodiodes, which convert light into electrical signals. Interposed between collimator 156 and grid 147 are two layers. One layer is a diode protection grid 158. A second layer 160 includes a checkerboard pattern. In one embodiment, layer 160 includes copper. Alternative embodiments do not include diode protection grid 158. Other alternative embodiments do not include second layer 160. Yet other embodiments do not include either of diode protection grid 158 or second layer 160. Since collimator 156 is externally mounted to detector module 122, collimator 156 can be easily removed and replaced, should it become damaged.

Detector module 122 includes multiple shields that include material such as lead for attenuating or blocking radiation from radiation source 112. Below substrate 150 is a top shield 148. Perpendicular to top shield 148 is a side shield 154. In the exemplary embodiment, there is one side shield 154 on each side of detector module 122. In addition, extending laterally from opposite sides of detector module 122 are wing shields, such as wing shield 152. Extending longitudinally from detector module 122 are mounting extensions 140, which facilitate aligning and mounting detector module 122 to gantry frame 114. Each mounting extension includes a groove 172 which allows detector module 122 to slide along a guide rail, as explained with reference to FIG. 11. Mounting pins 168 also facilitate aligning and securing detector module 122 in gantry frame 114.

Figure 8:
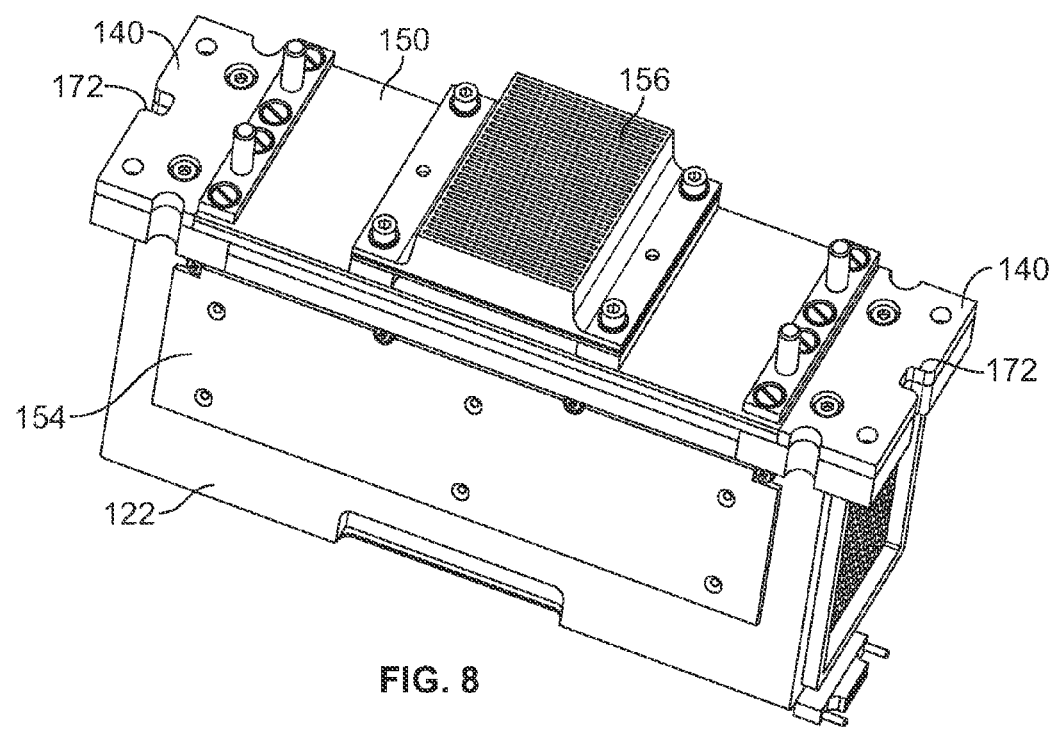
FIG. 8 is a perspective view of an exemplary detector module in accordance with the present invention.

FIG. 8 is another perspective view of detector module 122. In FIG. 8, collimator 156 is mounted to substrate 150, obstructing the view of diode protection grid 158 and checkerboard layer 160. Side shield 154 for attenuating or blocking radiation is visible. In some embodiments, one or more side shields are secured externally to an outer cover of detector module 122, while in other embodiments, one or more side shields are located within detector module 122. Yet other embodiments do not include a side shield at all. Mounting extensions 140 can be seen extending longitudinally from detector module 122.

Figure 9:
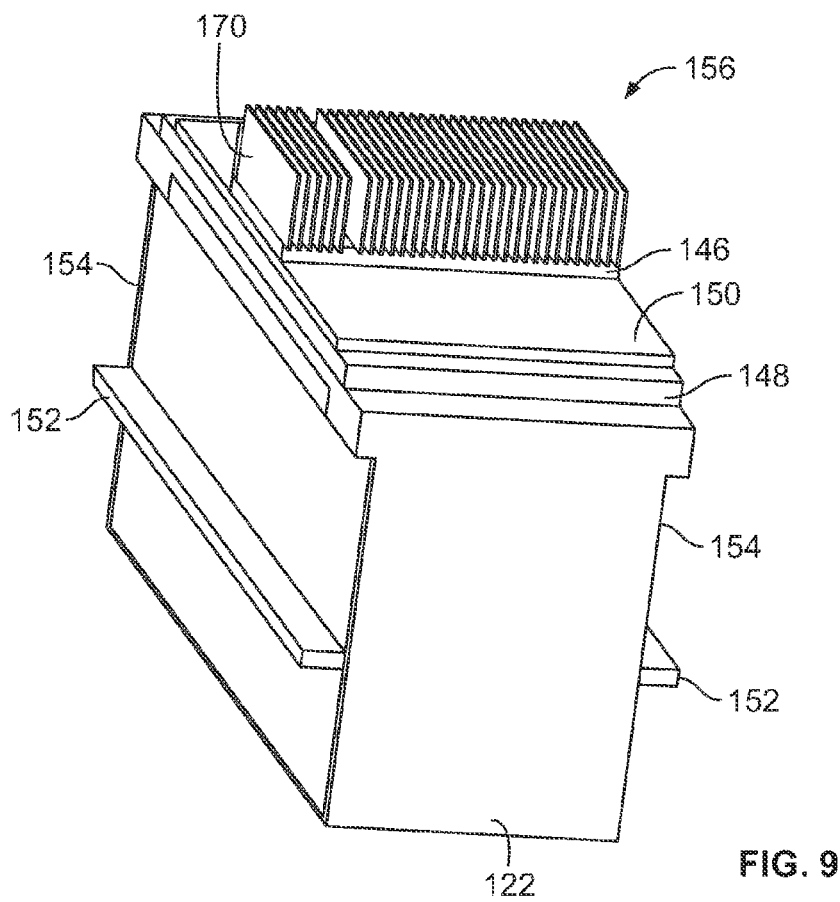
FIG. 9 is a simplified perspective view of an exemplary detector module in accordance with the present invention.

FIG. 9 is a simplified perspective view of detector module 122. As seen in FIG. 9, collimator 156 includes a plurality of fins, such as fin 170. Detector elements 146, which receive x-rays after the x-rays pass through collimator 156, include scintillators which convert ionizing radiation into light, and photodiodes, which convert light into electrical signals. Detector elements 146 are mounted to substrate 150. Top shield 148, side shields 154, and wing shields 152 block radiation and wing shields 152 block radiation that would otherwise pass between adjacent detector modules 122. However, between some detector modules 122 are gaps that cannot be completely filled by wing shields 152. In such cases, a gap-shield is located in the gap to block any radiation that would otherwise escape through the gap.

Figure 10:
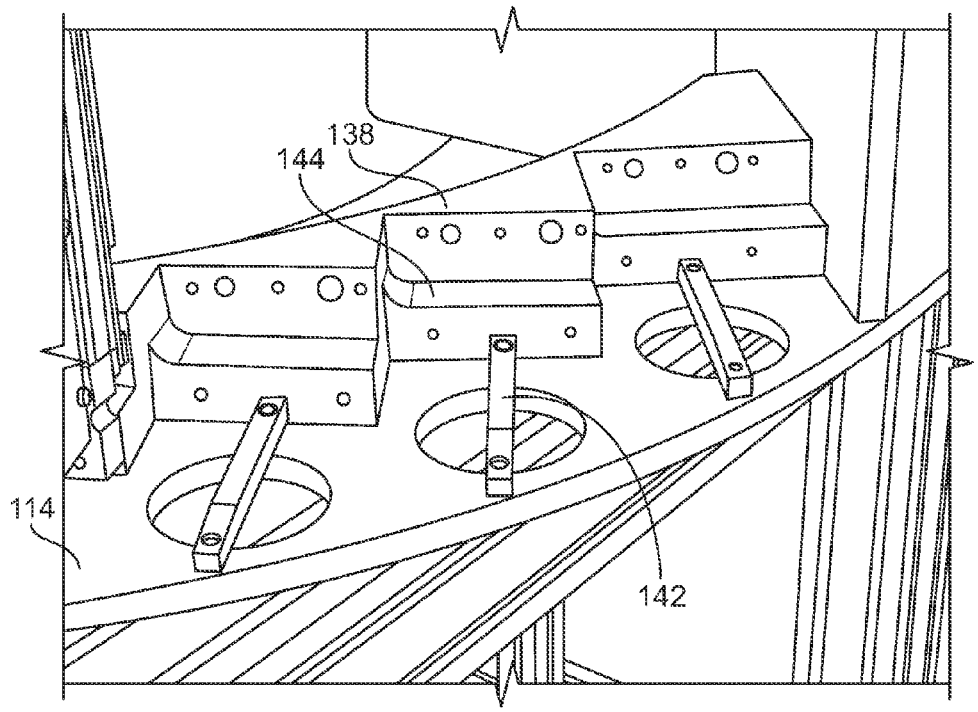
FIG. 10 is a perspective view of an exemplary gantry frame in accordance with the present invention, showing where detector modules are inserted into place.

FIG. 10 is a perspective view of exemplary gantry frame 114, illustrating attachment surfaces 144 where detector modules 122 are to be positioned along gantry frame 114. Positioning rail 138 includes multiple attachment surfaces 144, each corresponding to a location where detector element 122 is to be positioned. Extending from each attachment surface 144 is a guide rail 142.

Figure 11:
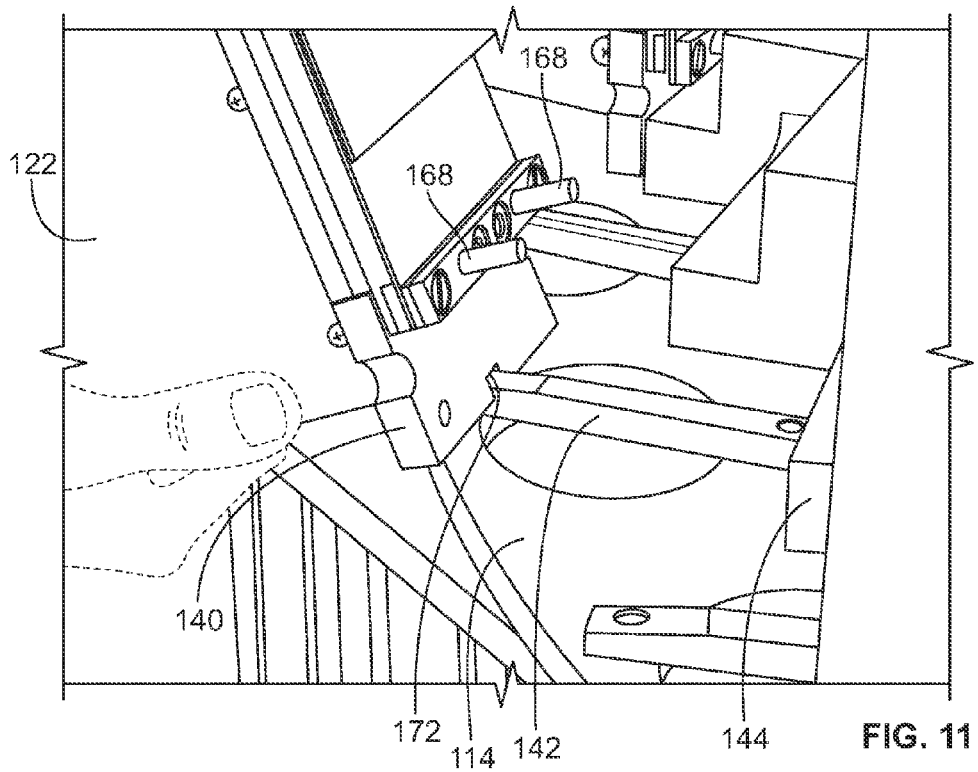
FIG. 11 is a perspective view of a detector module being aligned for insertion into the gantry frame, in accordance with an exemplary embodiment of the present invention.

FIG. 11 is a perspective view of detector module 122 being aligned for insertion into gantry frame 114. Mounting extension 140 includes groove 172, which slides over guide rail 142. By sliding groove 172 along guide rail 142, detector module 122 can be brought into alignment with corresponding attachment surface 144. Mounting pins 168 extend into corresponding holes in attachment surface 144 to assist in properly aligning detector module 122.

Figure 12:
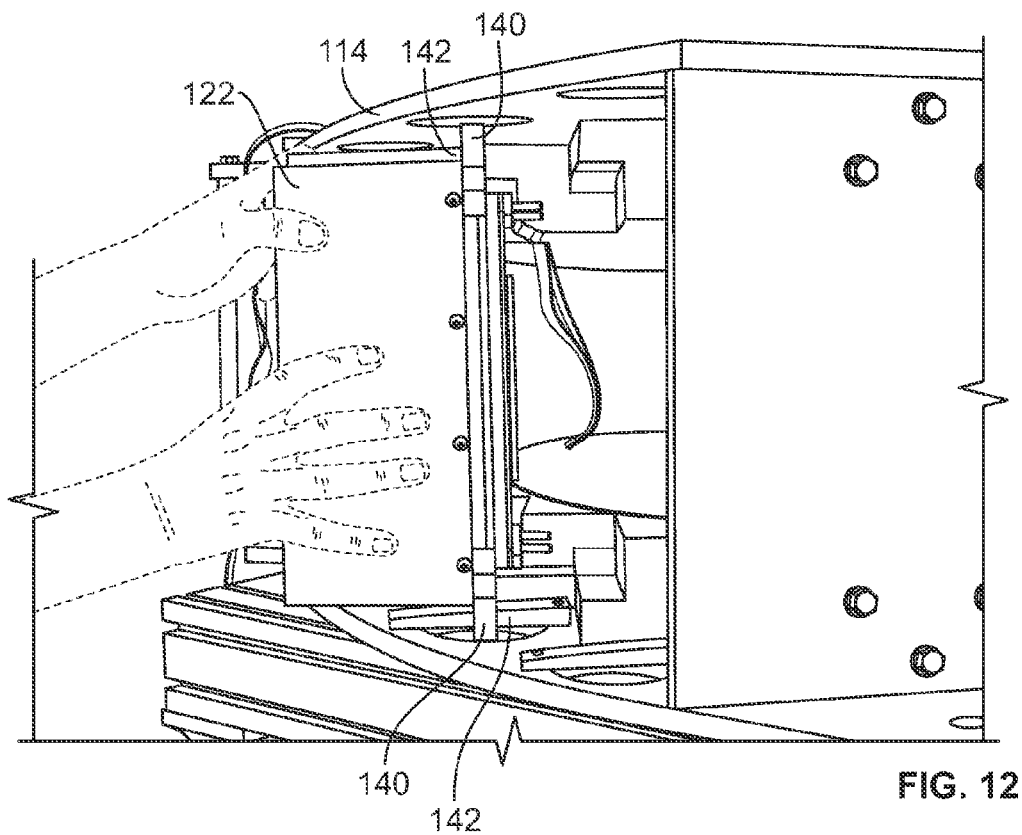
FIG. 12 is a perspective view of the detector module being inserted into the gantry frame, in accordance with the exemplary embodiment of the present invention.

FIG. 12 is a perspective view of detector module 122 being inserted into gantry frame 114. Shown in FIG. 12, both the bottom and top mounting extensions 140 have been lined up with corresponding guide rails 142 as detector module 122 is being slid along guide rails 142 to engage corresponding attachment surfaces 144.

Figure 13:
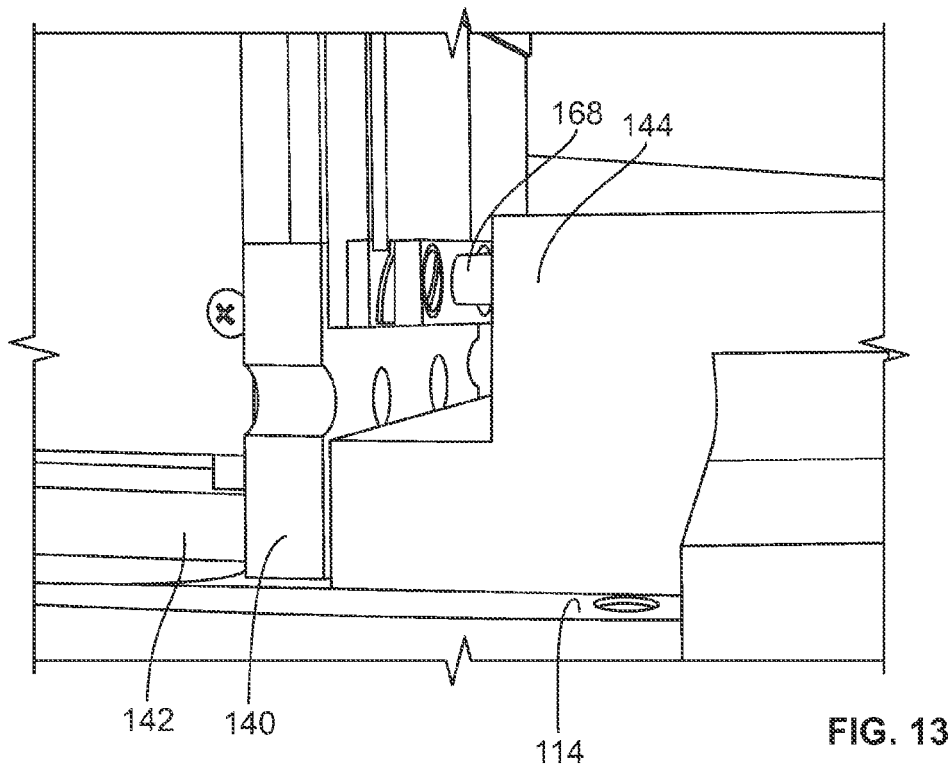
FIG. 13 is a perspective view showing the detector module secured in the gantry frame, in accordance with the exemplary embodiment of the present invention.

FIG. 13 is a perspective view showing detector module 122 secured in gantry frame 114. More specifically, each mounting extension 140 has been slid along a corresponding guide rail 142, and mounting pins 168 have engaged attachment surfaces 144. Detector module 122 can now be further secured to gantry frame 114 using screws or other fasteners.

Figure 14:
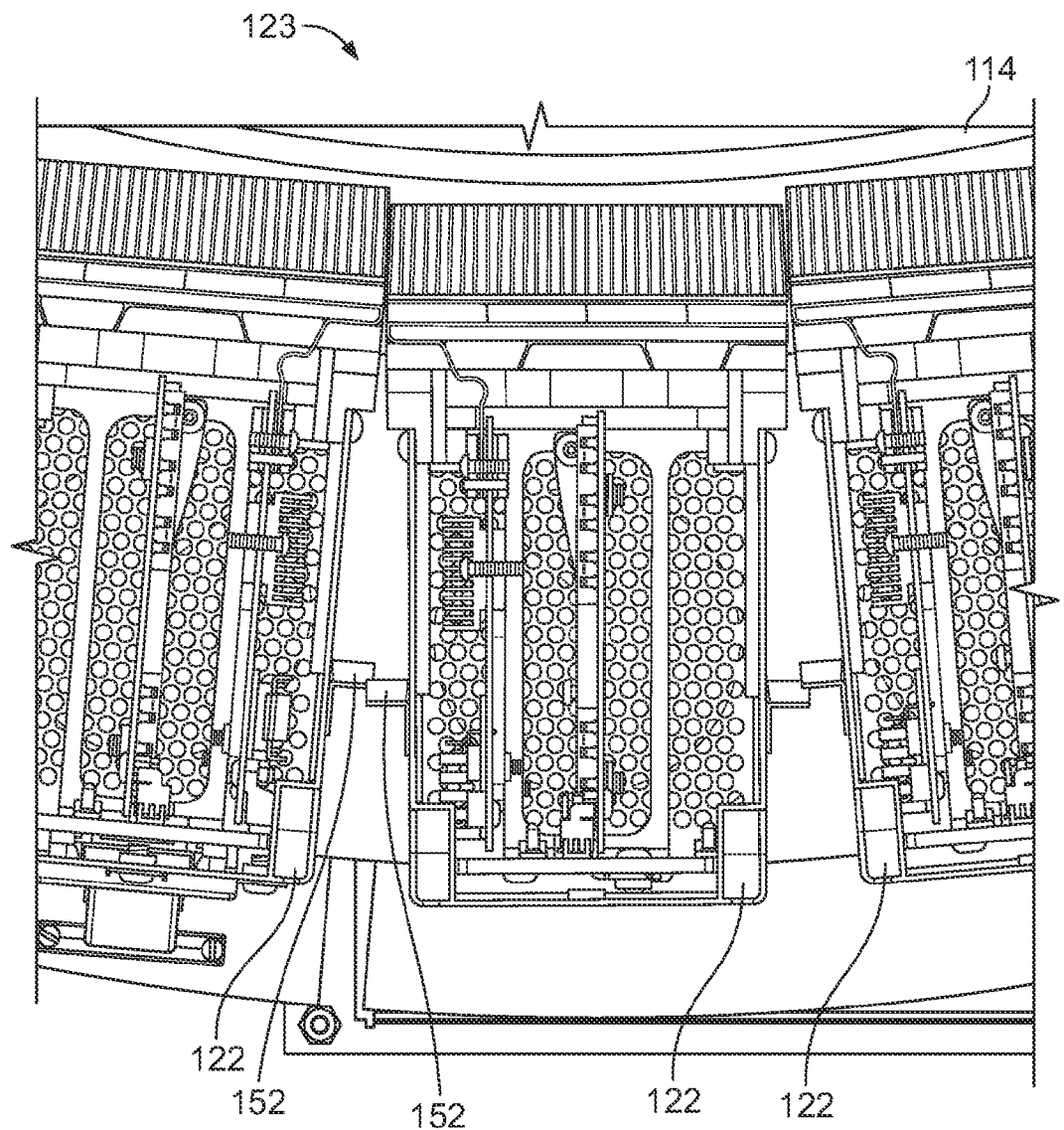
FIG. 14 is a side view showing detector modules located in the center of the array of detector modules, in accordance with the exemplary embodiment of the present invention.
Figure 15:
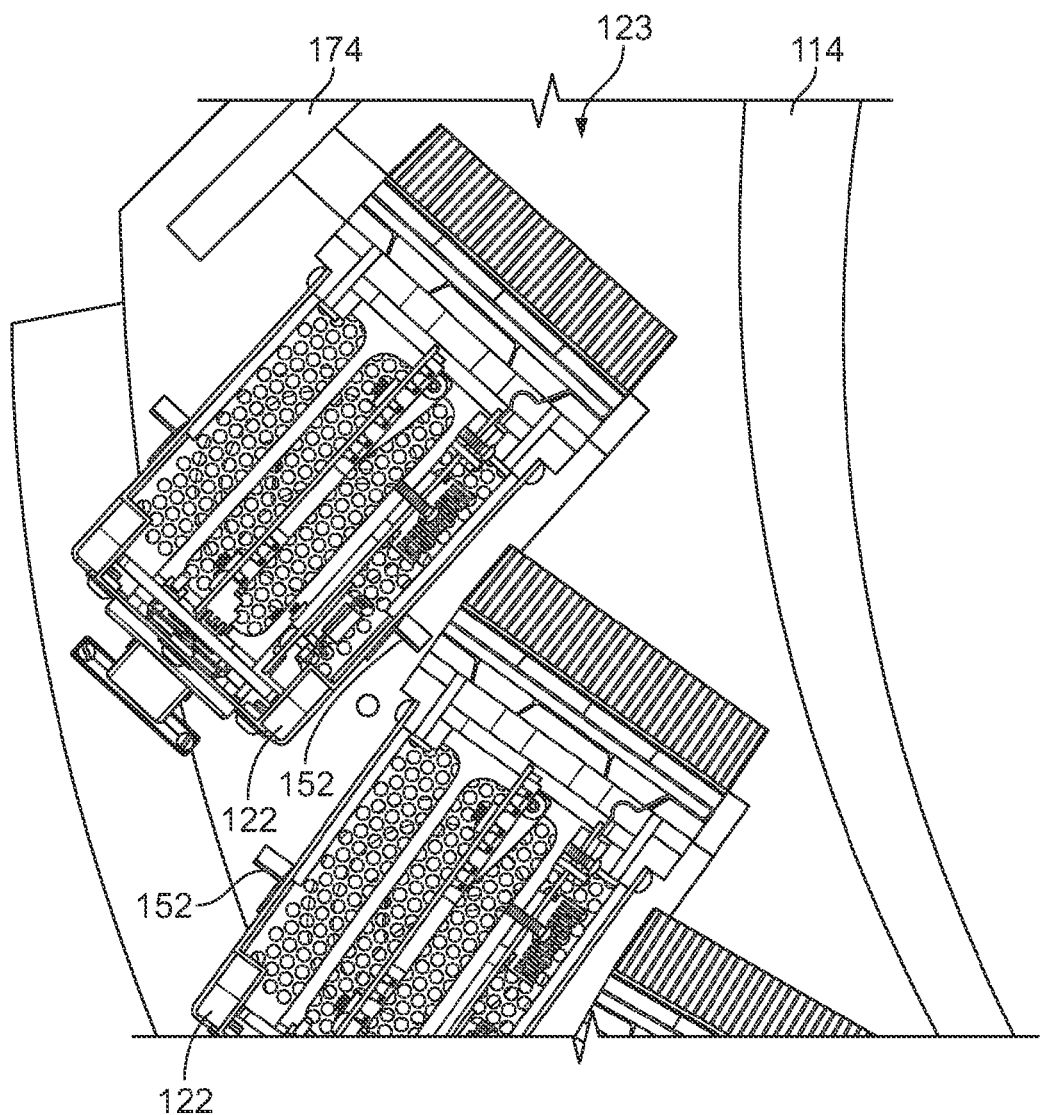
FIG. 15 is a side view showing detector modules located on one side of the array of detector modules, in accordance with the exemplary embodiment of the present invention.

FIG. 14 is a side view showing detector modules 122 located in the center of array 123 of detector modules 122 attached to gantry frame 114. As shown in FIG. 14, wing shields 152 of adjacent detector modules 122 are in close proximity to each other. FIG. 15 is a side view showing detector modules 122 located on first half 195 of array 123 of detector modules 122. Wing shields 152 are relatively far apart from each other, as compared to their proximity in FIG. 14. This illustrates the difference in angular spacing between detector modules 122 from the center of array 123 to the ends of array 123. Shield 172 is included on gantry frame 114 for blocking radiation from radiation source 114. Shield 172 includes a radiation-attenuating material, such as lead.

Figure 16:
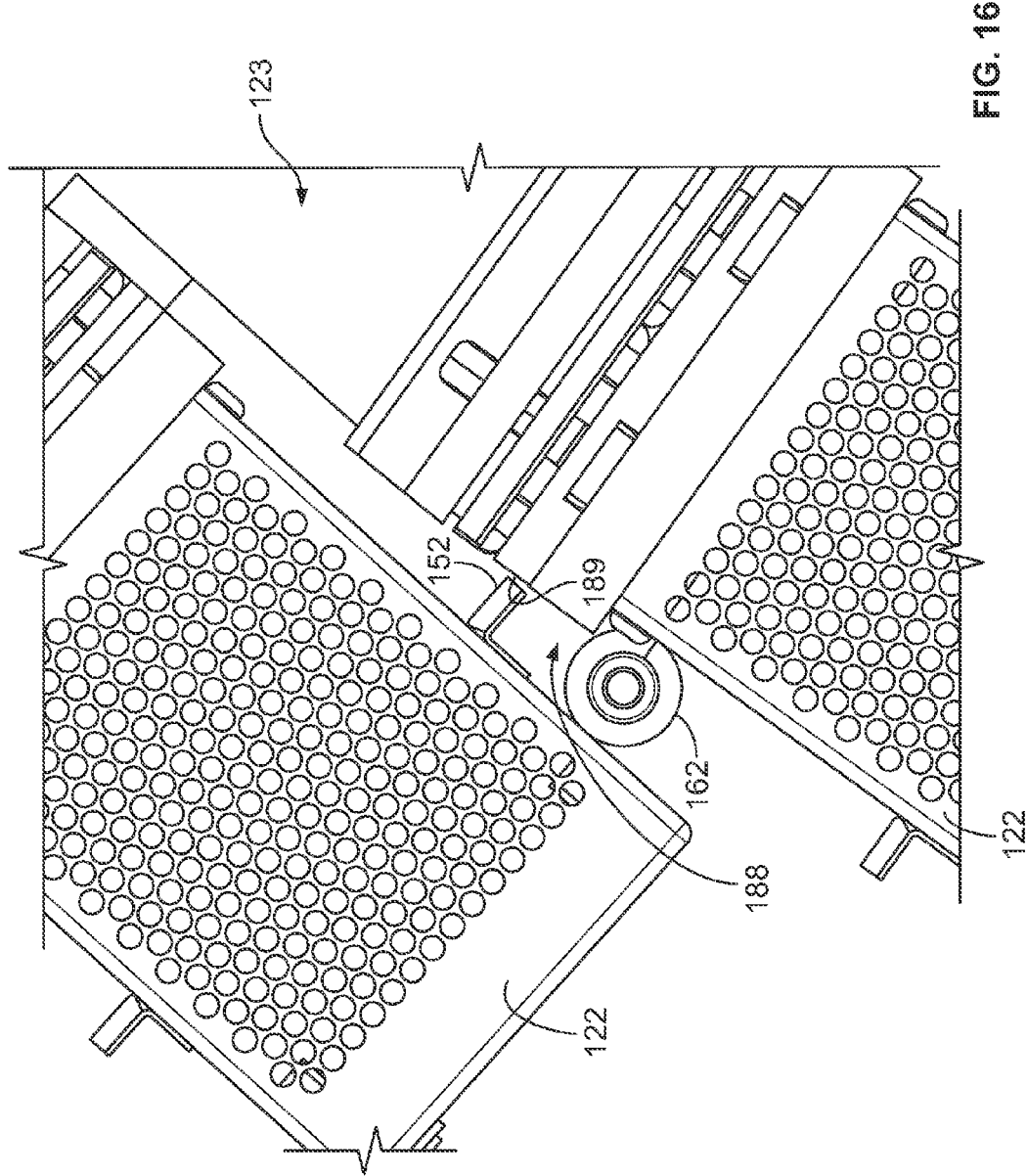
FIG. 16 is a side view showing a gap between two detector modules and a gap-shield located in the gap, in accordance with the exemplary embodiment of the present invention.

FIG. 16 is a side view showing a gap 188 between two adjacent detector modules 122 and a gap-shield 162 located in gap 188. As explained above, the angular spacing between adjacent detector modules increases moving towards either end of array 123 from the center. Accordingly, detectors closer to the ends of array 123 may have gaps between them that are not completely blocked by wing shields 152. As shown in FIG. 16, a gap 188 exists between wing shield 152 and a side 189 of detector module 122. Gap-shield 162 is located between two detector modules 122, thereby blocking radiation that might have passed through gap 188. Gap-shield 162 includes a radiation-attenuating material, such as lead.

Figure 17:
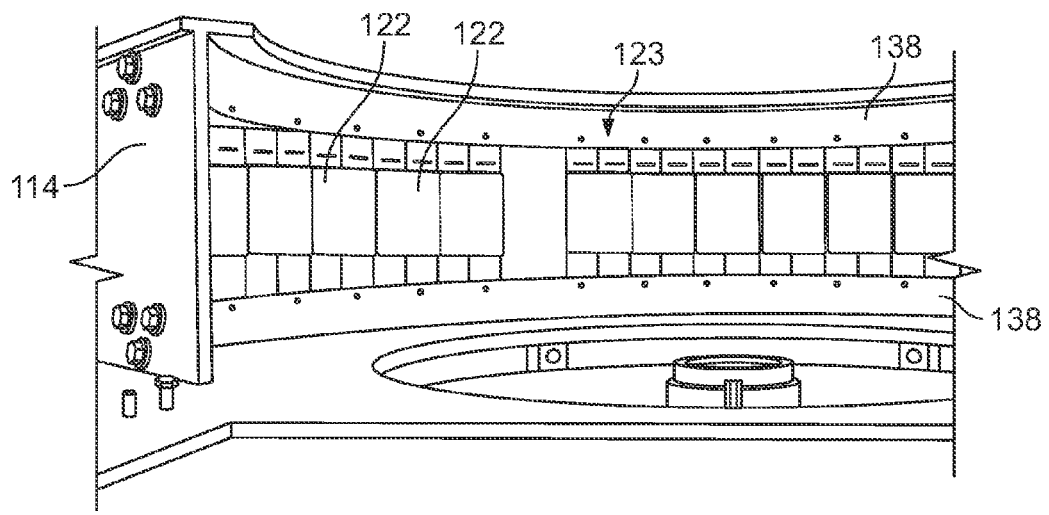
FIG. 17 is a perspective view showing a portion of the array of detector modules within the gantry frame, in accordance with the exemplary embodiment.

FIG. 17 is a perspective view showing a portion of array 123 of detector modules 122 within gantry frame 114. As shown in FIG. 17, detector module 122 is missing. However, since detector modules 122 are identical and interchangeable, a replacement detector module 122 can be readily inserted into position using guiding rails 138, as detailed above with reference to FIGS. 10 through 13.

Figure 18:
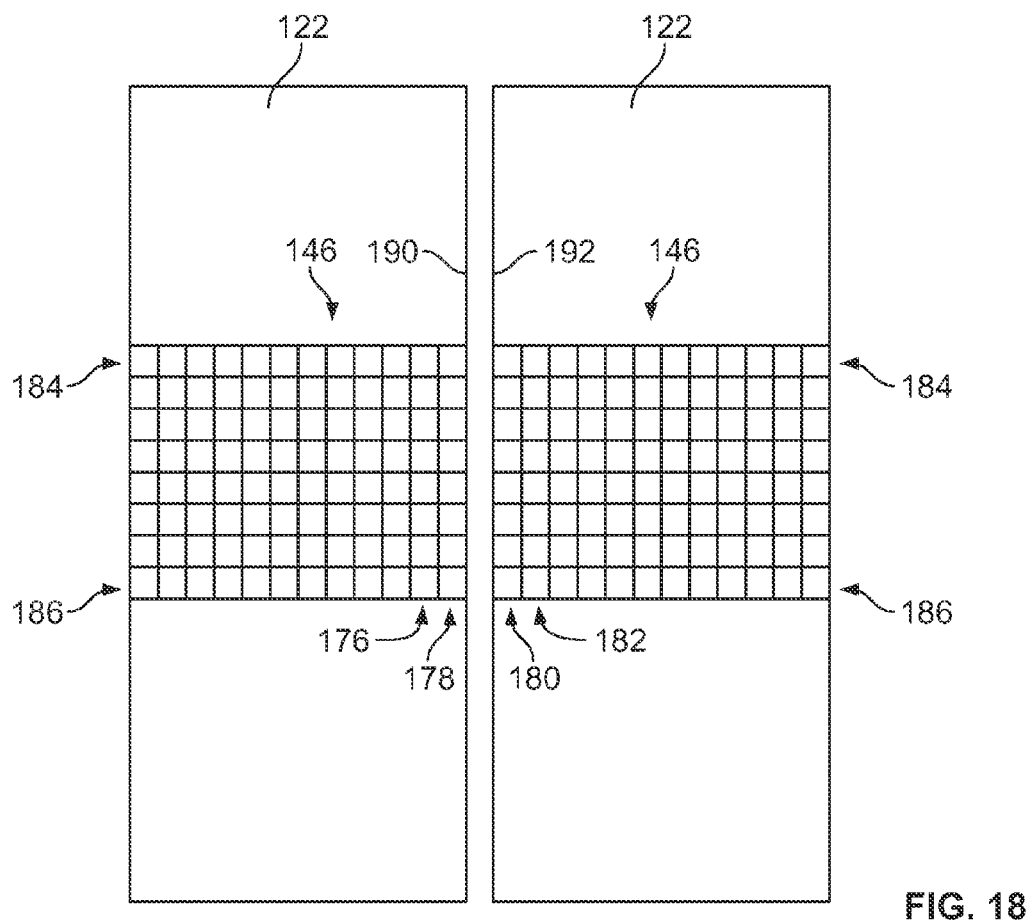
FIG. 18 is a simplified diagram showing detector elements on two adjacent detector modules, in accordance with an embodiment of the present invention.

FIG. 18 is a simplified diagram showing detector elements 146 on two adjacent detector modules 122. As shown in FIG. 18, adjacent detector modules 122 each include a top row 184 and a bottom row 186 of detector elements 146. Multiple rows exist between top row 184 and bottom row 186 as well. Detector elements 146 are also arranged in columns on each detector module 122. Columns 176 and 178 are located on the same detector module and are contiguous with each other. Likewise, columns 180 and 182 are located on the same detector module and are contiguous with each other. Column 178 is located on a first side 190 of left detector module 122, and is considered an "edge column." Likewise, column 180 exists on a second side 192 of adjacent detector module 122 and is also considered an "edge column."

Due to the compact geometry enabled by the configuration of detector modules 122 in gantry assembly 108, detector elements 146 arranged in columns along the edges of each detector module 122 have different effective collimation than their neighboring detector elements 146. This causes a differential scatter rejection in the measurements. The differential scatter signal present in these columns of detector elements 146 appears as an additive signal, in the intensity domain, that varies slowly as a function of time. The signal is predictable from the spatially-adjacent columns of detector elements 146, as the signal is also spatially low-frequency, with respect to the spatial pitch of detector elements 146 themselves. The differential scatter rejection results in strong image artifacts, if uncorrected. However, the location of these artifacts is known a priori within the measurement data, and the data associated with these columns of detector elements 146 is not missing. Rather, the data is only corrupted.

A predictor-corrector algorithm, which acts as a temporal recursive filter to estimate a correction based on neighboring columns of detector elements, can be used to correct the measured data from detector elements 146 located in columns along the edges of detector modules 122, for example columns 178 and 180. That is, the scatter signal in a given view is estimated using an adaptive filter that attempts to predict the differential scatter signal as a function of time using the past estimates and the current signals from spatially-neighboring columns of detector elements 146. Once the differential scatter is estimated, it is subtracted from the measurements to correct them. One exemplary embodiment of a process for correcting the artifacts is as follows:

1. A linear interpolation is used to calculate a predicted signal for an edge column. For example, if columns n, n+1 are edge columns on two adjacent detector modules, the prediction signal is made via a linear combination of columns n−1 and n+2. In some embodiments, columns n−1 and n+2 may be weighted differently from each other. In other embodiments, the two columns are given equal weight.

2. A scatter prediction for the current view and columns is used to correct the edge columns n, n+1, without using the predicted signal calculated above, in step 1.

3. The scatter prediction is updated using the difference between the corrected signal and the predicted signal from step 1. In some embodiments, the difference between the measurements is weighted by multiplying it by a coefficient.

The process will correctly restore, for example, the view of wires that pass through the scatter region, as the predictor has a limited slew rate. That is, only a fraction of the prediction error is fed back into the predictor. Thus, although a wire appears as a very large prediction error, it is very brief. Accordingly, the prediction filter does not react to the wire itself. On the other hand, general Compton scatter is a spatially low-frequency phenomenon, and is well-predicted from the spatially-neighboring columns of detector elements. Convergence of the filter is guaranteed in the steady state of a homogenous object.

The process uses a recursive filter to estimate the scatter contribution to an edge column, for example column 178, of detector elements 146, and updates that filter using the error between the corrected signal and the prediction based on the neighboring columns. The result is that small, high frequency perturbations, such as a metal wire, crossing the columns of detector elements located along edges of detector modules 122 are reconstructed correctly, and the correction based on the linear interpolation of data from neighboring detector elements 146 is only used to estimate the slowly varying scatter signal. While the above discussion provides an overview of the process, a more detailed description of an exemplary artifact-correcting process in accordance with the present invention is presented below.

Figure 20:
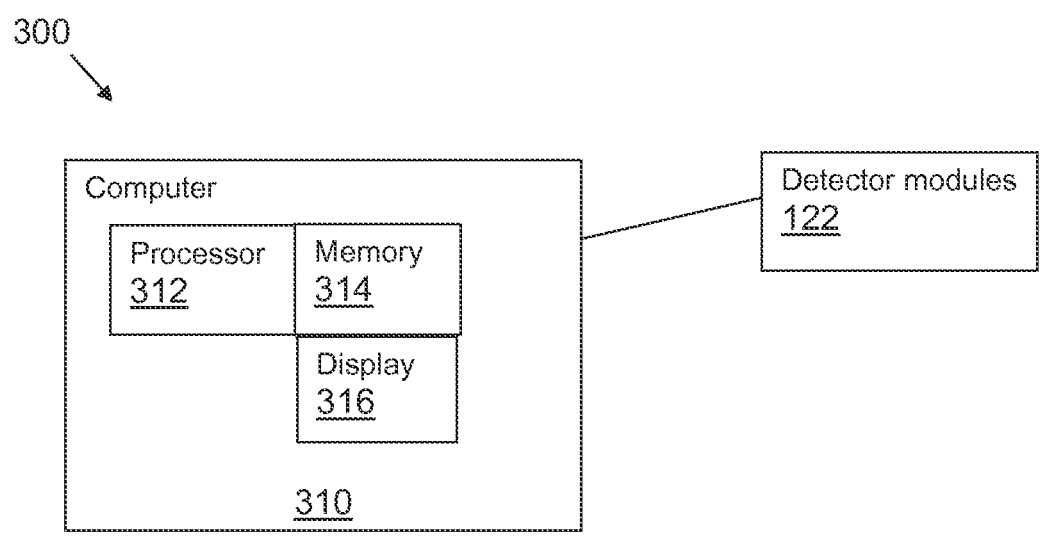
FIG. 20 is a block diagram of an exemplary embodiment of a computer communicatively coupled to detector modules to correct image artifacts in accordance with the present invention.

FIG. 20 is a block diagram 300 of a computer 310 communicatively coupled to detector modules 122. Computer 310 includes a processor 312, which is communicatively coupled to a memory 314 and a display 316. Stored in memory 314 is data received from detector modules 122 and instructions for carrying out a process of correcting artifacts in the data received from detector modules 122. Processor 312 is capable of executing the instructions stored in memory 314. Images may be displayed on display 316. Computer 310 may be physically separate from a baggage scanning system or integrated therein.

As can be seen from FIGS. 5 and 6, for example, array 123 of detector modules 122 includes first end 194 and second end 196 and is divided into first half 195 and second half 197. With reference to FIG. 18 and flowchart 200 shown in FIG. 19, if two detector modules 122 of FIG. 18 are located on first half 195 of array 123, the algorithm works as follows. First, data values from detector elements 146 in column 176 and data values from detector elements 146 in column 180 are added together and the sum is multiplied by 0.5. In other words, the values for columns 176 and 180 are averaged. These averaged values are considered predicted values for the data from detector elements 146 in column 178. This is shown as step 210 in FIG. 19. However, due to the above-discussed differential scatter rejection, the predicted values do not match the data that is actually measured by the detector elements 146 in column 178. A set of correction values for each detector element in column 178 exists in memory 314 of computer 310.

Figure 19:
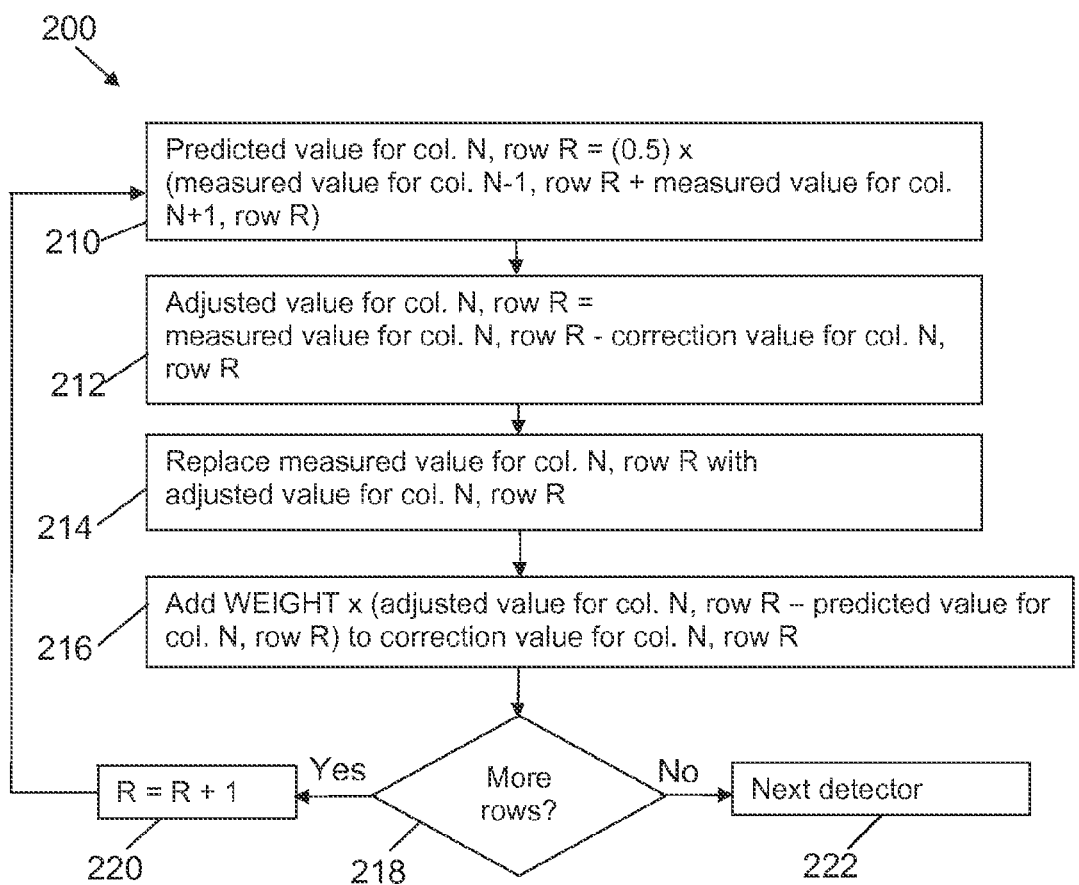
FIG. 19 is a flowchart of an exemplary embodiment of a process for correcting image artifacts in accordance with the present invention.

In the exemplary embodiment of the process, the correction values are initially zero. An adjusted value for the data corresponding to each detector element 146 in column 178 is calculated by subtracting a corresponding correction value from the measured value. This is shown as step 212 in FIG. 19. The measured value is then replaced by the adjusted value, as shown in step 214 in FIG. 19. Next, the difference between the predicted value and the adjusted value is added to the correction value for each detector element in column 178. This is shown as step 216 in FIG. 19. In some embodiments, the difference between the predicted value and the measured value is multiplied by a coefficient, shown as "WEIGHT" in step 216. The steps are performed on a row by row basis, as indicated by the determination of whether more rows exist at step 218. If there are more rows in the current detector module, then the process proceeds to step 220, wherein row index R is incremented and the process loops back to step 210 as shown in FIG. 19. If there are no more rows on the current detector module, the process proceeds to the next detector module in first half 195 of array 123 and repeats, as shown at step 222 in FIG. 19. As the steps discussed above are repeated, the correction values reach steady state. The coefficient "WEIGHT" shown in step 216 may be increased or decreased to adjust how quickly the correction values reach steady state.

A similar set of process steps are applied to detector modules 146 on second half 197 of array 123. Referring again to FIGS. 18 and 19, and assuming that two detector modules 122 shown in FIG. 18 are instead located on second half 197 of array 123, the process works as follows. First, data values from detector elements 146 in column 178 and data values from detector elements 146 in column 182 are added together and the sum is multiplied by 0.5. In other words, the values for the columns 178 and 182 are averaged. These averaged values are considered predicted values for the data from detector elements 146 in column 180. This is shown as step 210 in FIG. 19. However, due to the above-discussed differential scatter rejection, the predicted values do not match the data that is actually measured by detector elements 146 in column 180.

A set of correction values for each detector element 146 in column 180 exists in memory 314 of computer 310. In the exemplary embodiment, the correction values are initially zero. An adjusted value for the data corresponding to each detector element 146 in column 180 is calculated by subtracting the correction value from the measured value. This is shown as step 212 in FIG. 19. The measured value is then replaced by the adjusted value, as shown in step 214 in FIG. 19. Next, the difference between the predicted value and the adjusted value is added to the correction value for each detector element 146 in column 180. This is shown as step 216 in FIG. 19. Again, in some embodiments, the difference between the predicted value and the measured value is multiplied by a coefficient, shown as "WEIGHT" in step 216. The steps are performed on a row by row basis, as indicated by the determination of whether more rows exist at step 218. If more rows exist on the current detector module, the process proceeds to step 220, where the row index R is incremented and the process loops back to step 210 as shown in FIG. 19. If there are no more rows, the process proceeds to the next detector module and repeats, as shown at step 222 in FIG. 19. As the steps discussed above are repeated, the correction values reach steady state. As mentioned above, the coefficient "WEIGHT" shown in step 216 may be increased or decreased to adjust how quickly the correction values reach steady state.

The above-discussed process steps are performed on a row by row, detector module by detector module basis, in multiple passes. There is an initial period where each pass causes the correction values to be adjusted. Ultimately, however, the correction values reach steady state and, when subtracted from the measured data as discussed above, the image artifacts are removed.

It should be understood that processor as used herein means one or more processing units (e.g., in a multi-core configuration). The term processing unit, as used herein, refers to microprocessors, microcontrollers, reduced instruction set circuits (RISC), application specific integrated circuits (ASIC), logic circuits, and any other circuit or device capable of executing instructions to perform functions described herein.

It should be understood that references to memory mean one or more devices operable to enable information such as processor-executable instructions and/or other data to be stored and/or retrieved. Memory may include one or more computer readable media, such as, without limitation, hard disk storage, optical drive/disk storage, removable disk storage, flash memory, non-volatile memory, ROM, EEPROM, random access memory (RAM), and the like.

Additionally, it should be understood that communicatively coupled components may be in communication through being integrated on the same printed circuit board (PCB), in communication through a bus, through shared memory, through a wired or wireless data communication network, and/or other means of data communication. Additionally, it should be understood that data communication networks referred to herein may be implemented using Transport Control Protocol/Internet Protocol (TCP/IP), User Datagram Protocol (UDP), or the like, and the underlying connections may comprise wired connections and corresponding protocols, for example, Institute of Electrical and Electronics Engineers (IEEE) 802.3 and/or wireless connections and associated protocols, for example, an IEEE 802.11 protocol, an IEEE 802.15 protocol, and/or an IEEE 802.16 protocol.

A technical effect of systems and methods described herein includes at least one of: (a) calculating predicted values for image data associated with an edge column of a detector module based on image data associated with a first column and a second column, the first column and the second column being on opposite sides of the edge column; (b) calculating adjusted values for the image data associated with the edge column by subtracting correction values associated with the edge column from the measured values associated with the edge column; (c) replacing the measured values associated with the edge column with the calculated adjusted values; (d) increasing the correction values associated with the edge column based on the difference between the predicted values for the edge column and the correction values for the edge column.

Exemplary embodiments of the compact geometry CT system and methods for correcting image artifacts are described above in detail. The methods and systems are not limited to the specific embodiments described herein, but rather, components of systems and/or steps of the methods may be utilized independently and separately from other components and/or steps described herein. For example, the methods may also be used in combination with other imaging systems and methods, and are not limited to practice with only the compact geometry CT systems as described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An imaging system comprising:
   a rotating gantry;
   an x-ray source mounted to said gantry; and
   a plurality of interchangeable x-ray detector modules mounted to said gantry in a substantially annular arrangement, opposite said x-ray source, said plurality of detector modules having a center, said plurality of detector modules comprising a first detector module mounted at a first distance from said x-ray source, a second detector module mounted at a second distance from said x-ray source, and a third detector module mounted at a third distance from said x-ray source, wherein the first distance is different from the second distance, and wherein a first angular spacing between said first detector module and said second detector module is less than a second angular spacing between said second detector module and said third detector module, and wherein each detector module of said plurality of detector modules is configured to be bisected orthogonally by a corresponding radiation beam from said x-ray source, and wherein each said detector module comprises a collimator having a fixed focal length, and each said detector module is oriented such that said collimator in each said detector module is normal to the corresponding radiation beam from said x-ray source.

2. The imaging system of claim 1, wherein the third distance is different from the first distance and the second distance.

3. The imaging system of claim 1, wherein said plurality of detector modules comprises more than three detector modules.

4. The imaging system of claim 1, wherein each detector module comprises:
   a first planar layer comprising the collimator;
   a second planar layer comprising a plurality of detector elements;
   a third planar layer comprising a substrate; and
   a fourth planar layer comprising an x-ray attenuating shield,
   wherein said second planar layer is mounted between said first planar layer and said third planar layer, and said third planar layer is mounted between said second planar layer and said fourth planar layer.

5. The imaging system of claim 4, wherein each said detector module further comprises a plurality of x-ray attenuating side shields mounted to opposite sides of said detector module, and an x-ray attenuating wing shield extending laterally from each said x-ray attenuating side shield.

6. The imaging system of claim 1, wherein placement of said detector modules along a first side of the center is mirrored on the opposite side of the center.

7. The imaging system of claim 1, wherein the x-ray source includes a beam angle of approximately 90 degrees.

8. The imaging system of claim 1, having a resolution which is substantially uniform across said plurality of detector modules.

9. The imaging system of claim 1, wherein said imaging system is a computed tomography system.

10. The imaging system of claim 1, wherein said gantry is substantially annular.

11. The imaging system of claim 1, wherein said first detector module is at the center of the annular arrangement of the plurality of x-ray detector modules, said second detector module is adjacent said first detector module, and said third detector module is adjacent said second detector module.

12. A baggage scanning system comprising:
    a housing having a length, a first opening, and a tunnel, the first opening defining an entrance to said tunnel, said tunnel being oriented along the length of said housing;
    a conveyor located within said housing and oriented along the length of said housing;
    a gantry rotatably mounted within said housing, around said conveyor;
    an x-ray source mounted to said gantry; and
    a plurality of interchangeable x-ray detector modules mounted to said gantry in a substantially annular arrangement, opposite said x-ray source, said plurality of detector modules having a center, said plurality of detector modules comprising a first detector module mounted at a first distance from said x-ray source, a second detector module mounted at a second distance from said x-ray source, and a third detector module mounted at a third distance from said x-ray source, wherein the first distance is different from the second distance, and wherein a first angular spacing between said first detector module and said second detector module is less than a second angular spacing between said second detector module and said third detector module, and wherein each detector module is configured to be bisected orthogonally by a corresponding radiation beam from said x-ray source, and wherein each said detector module comprises a collimator having a fixed focal length, and each said detector module is oriented such that said collimator in each said detector module is normal to said corresponding radiation beam from said x-ray source.

13. The imaging system of claim 12, wherein the third distance is different from the first distance and the second distance.

14. The imaging system of claim 12, wherein said x-ray source emits a cone beam having a beam angle which intersects an entire cross section of said tunnel, the cross section being perpendicular to the length of said tunnel.

15. The imaging system of claim 12, further comprising a slip ring attached to said gantry and power, control, and data signals are transmitted to and from said gantry by said slip ring.

16. The imaging system of claim 12, wherein said gantry is configured to rotate continuously.

17. The baggage scanning system of claim 12, wherein said first detector module is at the center of the annular arrangement of the plurality of x-ray detector modules, said second detector module is adjacent said first detector module, and said third detector module is adjacent said second detector module.

18. A method of mounting interchangeable x-ray detector modules in a substantially annular arrangement, in a gantry of a computed tomography system to provide a compact geometry, the gantry including a substantially annular frame having a mounting point for an x-ray source, and a positioning rail located opposite the mounting point for the x-ray source, the positioning rail defining a plurality of attachment surfaces each corresponding to a mounting point for an interchangeable x-ray detector module, the interchangeable x-ray detector modules being adapted to mount to the attachment surfaces, the method comprising:

mounting a first interchangeable x-ray detector module at a first mounting point located a first distance from the x-ray source;

mounting a second interchangeable x-ray detector module at a second mounting point located a second distance from the x-ray source, wherein the first distance is different from the second distance; and mounting a third interchangeable x-ray detector module at a third mounting point located a third distance from the x-ray source, wherein a first angular spacing between the first interchangeable x-ray detector module and the second interchangeable x-ray detector module is less than a second angular spacing between the second interchangeable x-ray detector module and the third interchangeable x-ray detector module, wherein said second detector module is adjacent said first detector module, and said third detector module is adjacent said second detector module, and wherein each detector module is configured to be bisected orthogonally by a corresponding radiation beam from said x-ray source, and wherein each said detector module comprises a collimator having a fixed focal length, and each said detector module is oriented such that said collimator in each said detector module is normal to said corresponding radiation beam from said x-ray source.

\* \* \* \* \*